US006321909B1

(12) United States Patent
Wicomb et al.

(10) Patent No.: US 6,321,909 B1
(45) Date of Patent: *Nov. 27, 2001

(54) SYSTEM FOR STORING POLYETHYLENE GLYCOL SOLUTIONS

(75) Inventors: Winston Wicomb, Corte Madera; Geoffrey Collins, Belvedere; Ian Bathurst, Kensington; Matthew Foehr, San Francisco, all of CA (US)

(73) Assignee: Sky High, LLC, Evanston, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/022,500

(22) Filed: Feb. 12, 1998

Related U.S. Application Data

(60) Provisional application No. 60/065,586, filed on Nov. 18, 1997, provisional application No. 60/038,422, filed on Feb. 18, 1997, and provisional application No. 60/038,381, filed on Feb. 13, 1997.

(51) Int. Cl.[7] .................................................. A61B 19/00
(52) U.S. Cl. ........................................ 206/438; 206/524.4
(58) Field of Search ............................... 206/213.1, 438, 206/484, 484.2, 524.4

(56) References Cited

U.S. PATENT DOCUMENTS 3,728,839 * 4/1973 Glick ..................................... 206/63.3
3,815,315 * 6/1974 Glick ..................................... 206/63.3

(List continued on next page.)

FOREIGN PATENT DOCUMENTS

WO 87/00056   1/1987   (WO).
WO 94/13311   6/1994   (WO).
WO 94/25621   11/1994  (WO).
WO 95/15173   6/1995   (WO).

OTHER PUBLICATIONS

Hibbert et al. "Studies on reactions relating to carbohydrates and polysaccharides. LVI. The synthesis of the higher polyoxyethylene glycols" *J. Am. Chem. Soc.* (1993) 61:1905–1910.

Powell, III *Handbook of water–soluble gums&resins* (1980) R.L. Davidson (editor) McGraw–Hill Book Company, New York.

Delgado et al., "The uses and properties of PEG–linked proteins" *Critical Reviews in Therapeutic Drug Carrier Systems* (1992) 9:249–304.

Burnham "Polymers for delivering peptides and proteins" *Am. J. Hosp. Pharm.* (1994) 51:210–218.

(List continued on next page.)

*Primary Examiner*—David T. Fidei
(74) *Attorney, Agent, or Firm*—Sheridan Ross P.C.

(57) ABSTRACT

A composition comprising a storage-stable organ preservation solution, comprising a linear polyethylene glycol having an average molecular weight of approximately 20,000 Daltons and being essentially free of decomposition products. This solution can be used for organ preservation as a perfusate in a process in which the perfusate is flowed through the circulatory system of the organ, and can also be used for transplantation or routine open heart cardioplegic applications. The composition can be contained in a system comprising a means for preventing light exposure, especially UV light, to the solution. In addition, the system is preferably impervious to gases, particularly oxygen.

11 Claims, 5 Drawing Sheets

U.S. PATENT DOCUMENTS

| | | | | |
|---|---|---|---|---|
| 3,913,734 | * | 10/1975 | Siegel | 206/484 |
| 3,967,728 | * | 7/1976 | Gordon et al. | 206/423 |
| 4,018,222 | * | 4/1977 | McAleer et al. | 206/365 |
| 4,135,622 | * | 1/1979 | Glick | 206/484 |
| 4,140,678 | * | 2/1979 | Shalaby et al. | 206/63.3 |
| 4,227,615 | * | 10/1980 | Flick . | |
| 4,322,403 | * | 3/1982 | Bunning | 424/85 |
| 4,449,631 | * | 5/1984 | Levenburg et al. | 206/484 |
| 4,597,765 | * | 7/1986 | Klatt | 206/438 |
| 4,732,863 | | 3/1988 | Tomasi et al. | 436/547 |
| 4,741,903 | * | 5/1988 | Smith | 424/94.63 |
| 4,762,124 | * | 8/1988 | Kerch et al. | 206/438 |
| 4,902,502 | | 2/1990 | Nitecki et al. | 424/83 |
| 4,919,272 | * | 4/1990 | Kai et al. | 206/484 |
| 4,938,961 | | 7/1990 | Collins et al. | 424/606 |
| 5,006,118 | * | 4/1991 | Yule | 604/408 |
| 5,089,261 | | 2/1992 | Nitecki et al. | 424/85.2 |
| 5,197,618 | * | 3/1993 | Goth | 206/484.2 |
| 5,230,427 | * | 7/1993 | Betts et al. | 206/213.1 |
| 5,334,382 | * | 8/1994 | Phillips et al. | 424/94.3 |
| 5,370,989 | * | 12/1994 | Stern et al. | 435/1 |
| 5,447,722 | | 9/1995 | Lang et al. | 424/280.1 |
| 5,532,150 | * | 7/1996 | Snow et al. | 435/188 |
| 5,536,251 | | 7/1996 | Evard et al. | 604/93 |
| 5,559,213 | | 9/1996 | Hakimi et al. | 530/351 |
| 5,595,732 | | 1/1997 | Hakini et al. | 424/85.7 |
| 5,613,937 | | 3/1997 | Garrison et al. | 600/201 |
| 5,618,306 | | 4/1997 | Roth et al. | 606/205 |
| 5,618,307 | | 4/1997 | Donlon et al. | 606/205 |
| 5,626,607 | | 5/1997 | Malecki et al. | 606/205 |
| 5,681,740 | * | 10/1997 | Messier et al. | 206/438 |
| 5,763,028 | * | 6/1998 | Matsumoto et al. | 206/484.2 |

OTHER PUBLICATIONS

Wicomb "Advances in heart storage" *The Transplantation and replacement of thoracic organs, 2$^{nd}$ edition* (1997) D.K.C Cooper (editor) Kluwer Academic Publishers, The Netherlands.

Kluwer Academic Publishers Group. Letter from publisher confirming publication date of the above.

Collins et al. "New organ preservation solutions" *Kidney Internationa l*(1992) 42:S–197–S–202.

Belzer et al. "Principles of solid–organ preservation by cold storage" *Transplantation* (1988) 45:673–676.

Wicomb et al. "Comparison of cardioplegic and UW solutions for short–term rabbit heart preservation" *Transplantation* (1987) 47:733–734.

Wicomb et al. "Value of polyethylene glycol (PEG) and horseradish peroxidase (HRP) for hypothermic rabbit heart perfusion" Transplantation Proceedings (1989) 21:1366–1368.

Wicomb et al. "24–hour rabbit heart storage with UW solution" *Transplantation* (1989) 48:6–9.

Wicomb et al. "Optimal cardioplegia and 24–hour heart storage with simplified UW solution containing polyethylene glycol" *Transplantation* (1990) 49:261–264.

Collins et al. "Heart preservation solution containing polyethyleneglycol: an immunosuppressive effect?" *The Lancet* (1991) 338:890.

Mack et al. "Effect of polyethylene glycol on lipid peroxidation in cold–stored rat hepatocytes" *Cryobiology* (1991) 28:1–7.

Schmid et al. "The use of myocytes as a model for developing successful heart preservation solutions" *Transplantation* (1991) 52:20–26.

Wicomb et al. "Twenty–four–hour ice storage of rabbit heart" *The Journal of Heart and Lung Transplantation* (1994) 13:891–894.

Itasaka et al. "Modification of rejection by polyethylene glycol in small bowel transplantation" *Transplantation* (1994) 57:645–648.

Tokunaga et al. "The immunosuppressive effect of polyethylene glycol in a flush solution for atr liver transplantation" *Transplantation* (1992) 54:756–758.

Guyton, A.C., *Basic human physiology* (1997) W.B. Saunders Company, Philadelphia, Pennsylvania.

Ferreira et al. "Effect of supplementing cardioplegic solution with deferoxamine on reperfused human myocardium" *J. Thorac. Cardiovacs. Surg.* (1990) 100:708–714.

Borg et al. "Prooxidant action of desferrioxamine fenton–like production of hydroxyl radicals by reduced ferrioxamine" *Journal of Free Radicals in Biology & Medicine* (1986) 2:237–243.

Chien et al. "Hibernation induction trigger for organ preservation " *Medical Intelligence Unit* (1993) .

Wicomb et al. "Forty–eight hours hypothermic perfusion storage of pig and baboon hearts" *Journal of Surgical Research* (1986) 40:276–284.

Simpson "Stimulation of hypertrophy of cultured neonatal rat heart cells through an $\alpha_1$– and $\beta_1$–adrenergic receptor interaction" *Circulation Research* (1985) 56:884–894.

Holdefer et al. "Cardiotonic effects of reduced sulfhydryl amine after preservation of rabbit hearts" *The Journal of Heart and Lung Transplantation* (1994) 13:17–159.

Wicomb et al. "Improved cardioplegic using new perfusates" Transplantation Proceedings (1989) 21:1357–1358.

Al–Abudulla et al. "The effects of supercooling chemicals on myocardial ultrastructure: a transmission electron microscopy case study" *Connecticut Medicine* (1995) 59:387–399.

Bauza et al. "Metabolic and functional effects of polyethylene glycol 20M and 2,3–butanedione monoxime during single flush or oxygenated microperfusion preservation: comparison with plegisol" Transplantation Proceedings (1996) 28:284–285.

Itasaka et al. "Effect of polyethylene glycol on rat small bowel rejection" Transplantation Proceedings (1992) 24: 1179–1180.

Marsh et al. "Hypothermic preservation of hepatocytes" *Cryobiology* (1989) 26: 524–534.

Poullain et al. "Viability and primary culture of rat hepatocytes after hypothermic preservation: the superiority of the Leibovitz Medium over the University of Wisconsin solution for cold storage" *Hepatology* (1992) 15:97–106.

Tokunaga et al. "Effects of polyethylene glycol on rat liver allograft rejection" *Hepatology* (1991) 14:228(A).

Wicomb et al. "Experimental and clinical evaluation of a new polyethylene glycol (PEG20M) solution for cardiac preservation" *The Journal of Heart Transplantation* (1990) 9:78(A).

Wicomb et al. "The role of reduced glutathione in heart preservation using a polyethylene glycol solution, cardiosol" *Transplantation* (1992) 54:181–182.

Zheng et al. "Prolonged pancreas preservation using a simplified UW solution containing polyethylene glycol" *Transplantation* (1991) 51:63–66.

Avigad "A simple spectrophotometric determination of formaldehyde and other aldehydes: application to periodate–oxidized glycol systems" *Analytical Biochemistry* (1983) 134:499–504.

Wicomb et al. "Choice of cation in solutions for hypothermic storage of liver and heart" *Transplantation* (1991) 51:281–282.

Wicomb et al. "Donor heart preservation–limitations of cardioplegia and warm ischemia" *Transplantation* (1992) 53:947–948.

Han et al., 1997, *Polymer*, 38(2):317–323.

Imamura et al., 1981, *Bull. Chem. Soc. Jpn.*, 54(5):1548–1553.

Itasaka et al., 1994, *Transplantation*, 57(5):645–648.

Kadish et al., 1983, *Hybridoma*, 2(1):87–89.

* cited by examiner

SYSTEM FOR STORING POLYETHYLENE GLYCOL SOLUTIONS

CROSS-REFERENCE TO RELATED APPLICATIONS

This application claims priority to U.S. provisional Application Nos. 06/038,381, filed Feb. 13, 1997, 06/038,422, filed Feb. 18, 1997, and 06/065,586, filed Nov. 18, 1997.

STATEMENT OF RIGHTS TO INVENTIONS MADE UNDER FEDERALLY SPONSORED RESEARCH (Not Applicable)

TECHNICAL FIELD

This invention relates to biologically effective compositions of matter containing substantially linear polyethylene glycol (LPEG) and methods of use thereof. Specifically, it relates to organ protection, preservation and cardioplegic solutions and methods of use thereof in surgical operations on and transplantation of mammalian organs.

BACKGROUND

Polyethylene glycol.

Polyethylene glycol ("PEG"), (α-Hydro-ω-hydroxypoly(oxy-1,2-ethanediyl)), is known by numerous designations including macrogol; PEG; Carbowax; Jeffox; Nycoline; Pluracol E; Poly-G; Polyglycol E; and Solbase. PEG refers to the liquid and solid polymers of the general formula $H(OCH_2—CH_2)_nOH$, where n is greater or equal to 4. In general, each PEG is followed by a number which corresponds to its average MW. Its synthesis is described for instance in Hibbert (1939) *J. Am. Chem. Soc.* 61:1905–1910. For review see Powell, III in *Handbook of Water-Soluble Gums & Resins,* R. L. Davidson ed. (McGraw-Hill, New York, 1980) pp. 18/1–18/31. PEGs have found use as water-soluble lubricants for rubber molds, textile fibers, and metal-forming operations, in food and food packaging, in hair preparations and in cosmetics in general and as ointment and suppository bases in pharmaceutical compositions.

Typically, PEGs are clear, viscous liquids or white solids that dissolve in water to form transparent solutions. They are soluble in many organic solvents and readily soluble in aromatic hydrocarbons. They are only slightly soluble in aliphatic hydrocarbons. Typically, they do not hydrolyze on storage. PEGs have low toxicity. PEG20M consists of two or more molecules of PEG having approximate molecular weights of 6000–10,000 joined by a bisphenol epoxide linker (CAS # 37225-26-6; CAS name Oxirane, 2,2'[(1-methyl-ethylidene)bis(4,1-phenyleneoxy methylene)]bis-, polymer with α-hydro-ω-hydroxypoly(oxy-1,2-ethanediyl). PEG20L is a substantially linear PEG having an average molecular weight of about 20,000 Daltons (available from several commercial sources including, but not limited to, Clariant/Hoechst Celanese, Fluka and Nippon Oils and Fats). The molecular weights of PEG compositions listed herein are given in number averages rather than weight averages. Various other molecular weights of linear PEG are also available from several commercial sources.

More recently, PEG has been used in a number of pharmacologic applications. The conjugation of PEG to foreign proteins, such as cytokines and antibodies, reduces the immune response triggered when the proteins are administered into test mammals. U.S. Pat. Nos. 5,447,722; 4,902,502; 5,089,261; 5,595,732; 5,559,213; and 4,732,863. Conjugation to PEG also increases the solubility and biological half-life of cytokines. WO 8700056 and U.S. Pat. No. 5,089,261. Conjugates of PEG and glucocerebroside have been formulated for treating Gaucher's disease. WO 9413311. PEG has also been conjugated to such enzymes as adenosine deaminase, amidase bovine and asparaginase, for therapeutic use. See Delgado et al. (1992) *Crit. Rev. Ther. Drug. Carrier Syst.* 9:249–304; and Burniam (1994) *Am. J. Hosp. Pharm.* 51:210–218, for review.

Organ preservation solutions.

Transplantation of vital organs such as the heart, liver, kidney, pancreas, and lung has become increasingly successful and sophisticated in recent years. Because mammalian organs progressively lose their ability to function during storage, even at low temperatures, transplant operations need to be performed expeditiously after organ procurement so as to minimize the period of time that the organ is without supportive blood flow.

In clinical practice, the two major situations in which cardiac preservation is required are heart transplantation and cardioplegia for open heart surgery. In heart transplantation, the donor heart is exposed through a midline sternotomy. After opening the pericardium, the superior and inferior vena cavae and the ascending aorta are isolated. The venous inflow is then occluded, the aorta is cross clamped, and approximately 1 liter of cold cardioplegic solution is flushed into the aortic root under pressure through a needle. As a result, the heart is immediately arrested, and cooling is supplemented by surrounding it with iced saline. The cold, arrested heart is then surgically excised, immersed in cold cardioplegic solution, packed in ice and rushed to the recipient.

The recipient's chest is opened through a midline sternotomy, and after placing the patient on cardiopulmonary bypass, the diseased heart is excised. The preserved donor heart is then removed from the preservation apparatus, trimmed appropriately and sewn to the stumps of the great vessels and the two atria in the recipient chest. After completion of the vascular anastomoses, blood is allowed to return to the heart. The transplanted heart will then either resume beating spontaneously or will require chemical and electrical treatment to restore normal rhythm. When the heart is ready to take over the circulation, the cardiopulmonary bypass is discontinued and the recipient's chest closed.

Most non-transplant surgical procedures on the heart, such as coronary artery bypass grafting, require that the heart beat be arrested for a period ranging from approximately 30 minutes to 120 minutes. The elective stopping of cardiac activity temporarily by injection of chemicals, selective hypothermia or electrical stimuli is termed "cardioplegia." During the period of arrest, the heart is kept cool by external cooling as well as by periodically reflushing a cardioplegic solution through the coronary arteries. The composition of the cardioplegia solution is designed to rapidly arrest the heart and to keep it in good condition during the period of standstill so that it will resume normal function when the procedure is finished.

In these cardioplegic procedures, the heart is exposed in the chest, and at a minimum, the aortic root is isolated. A vascular clamp is applied across the aorta and approximately 1 liter of cold cardioplegic solution is flushed into the aortic root through a needle. Venting is provided through the left ventricle, pulmonary artery or the right atrium and the effluent cardioplegic solution, which may contain high levels of potassium, is sucked out of the chest. This, together with external cooling, produces rapid cessation of contractions. During the period of arrest, the patient's circulation is maintained artificially using cardiopulmonary bypass. If the level of potassium in the cardioplegic solution is sufficiently high, bi-caval cannulation can be used to prevent the build up of potassium in the body that could interfere with later attempts to restart contractions in the heart.

After completion of the surgical procedure, blood flow is restored to the coronary circulation and heartbeat either returns spontaneously or after chemical and electric treatment. The ease with which stable function is restored depends to a large extent on the effectiveness of preservation by the cardioplegic solution. Once the heart is beating satisfactorily, cardiopulmonary bypass is discontinued and the chest eventually closed. General methods for organ transplant and heart surgery are disclosed in D. K. C. Cooper (editor), *The Transplantation and Replacement of Thoracic Organs,* Boston, Kluwer Academic Publishers (1997); and Collins et al. *Kidney International* 42:S-197-S-202 (1992) and the art cited therein, and are commonly known in the art.

It is generally understood that "living" organs, including the heart, continue the process of metabolism after removal from the donor so that cell constituents are continuously metabolized to waste products. If the organ storage technique is inadequate, the accumulation of these metabolic waste products, depletion of cell nutrients and consequent change in cell composition lead to progressive loss of function and ultimately to cell death. That is, the organ will lose its ability to function adequately after transplantation into the recipient. Several procedures have been explored to successfully enable organ preservation ex vivo for useful time periods. In one method, the donor organ is cooled rapidly by flushing cold solutions through the organ's vascular system and maintaining the organ at temperatures near 0° C. for the purpose of greatly slowing the metabolic rate. In the case of the mammalian heart, the flush solution composition is designed to quickly cause the heart to stop beating as well as to preserve it.

In 1988, University of Wisconsin (UW) solution was described. Belzer et al. *Transplantation* 45:673–676 (1988). This solution, capable of preserving the pancreas and kidney for 72 hours, and the liver for 30 hours, subsequently became the standard organ preservation solution (OPS) for transplant surgery and the benchmark against which other OPS compositions were measured. However, the heart is more recalcitrant to long-term storage than other organs, and UW solution is unreliable for storage of hearts for as short a period as 24 hours. Wicomb et al. *Transplantation* 47:733–734 (1989).

Improvements in the design of OPS compositions, as reviewed in Collins et al. *Kidney, International* 42:S-197-S-202 (1992) and others described in the art, have proceeded along several paths, including: (1) modification and simplification of UW solution; (2) investigation of organ-specific requirements; (3) addition of pharmacologic agents, particularly calcium antagonists for control of acidosis; (5) the use of a terminal rinse solution; and (6) the use of solutions containing polyethylene glycol (PEG).

Wicomb et al. reported the beneficial effects of PEG 8000 on rabbit hearts preserved by oxygenated low pressure perfusion for 24 hours; this solution also contained horseradish peroxidase. Wicomb et al. *Transplantation Proceedings* 21:1366–1368 (1989). The substitution of PEG20M for hydroxyethyl starch (HES) as the colloid in UW solution also yielded excellent cardiac function. The substitution of PEG20M for HES also allowed rabbit heart storage up to 24 hours by microperfusion. Wicomb et al. *Transplantation* 48:6–9 (1989).

An improved OPS, "PEG20M-Cardiosol™" used as a heart preservation solution, contained the substitution of PEG20M for HES and eliminated five components of UW solution (penicillin, dexamethasone, insulin, allopurinol, and adenosine). Wicomb et al. *Transplantation* 49:261–264 (1990); and U.S. Pat. No. 4,938,961, issued Jul. 3, 1990 to Collins et al. That heart preservation solution contains 5% or 10% by weight polyethylene glycol 20M (Union Carbide Chemicals and Plastics Co., Inc., Charleston, W. Va.), 40 mM sodium, 125 mM potassium, 5 mM magnesium, 25 mM phosphate, 5 mM sulfate, 100 mM lactobionate, 30 mM raffinose, and 3 mM glutathione. Collins et al. *The Lancet* 338:890–891 (1991). This solution was found to be superior to UW solution both for 4-hour hypothermic and 24-hour microperfusion storage. Collins et al. (1992). "Microperfusion" is a hypoxie, very-low-flow perfusion with flowrates such as 3 ml/g heart wt/24 hour, which is 1/500 of that typical of conventional continuous perfusion. Wicomb et al. *Transplantation* 48:6–9 (1989).

The superiority of PEG in preservation solutions remains widely accepted. Mack et al. *Cryobiology* 28:1 (1991); Malhotra et al. *Transplantation* 52:1004 (1991); and Schmid et al. *Transplantation* 52:20 (1991). A solution containing polyethylene glycol 20 L has been studied for its effect on rejection of transplanted small bowel allografts. Wicomb et al. *J. Heart Lung Transplantation* 13:891–894 (1994). While the solution was apparently active as an immunosuppressant in small bowel transplant, prolonged survival was not related to improved preservation and no correlation was seen between recovery and the type of flush solution used. Wicomb et al. *J. Heart Lung Transplantation* 647 (1994).

The mechanism of PEG activity in OPS in unknown. However, as reviewed in Collins et al. (1992), PEG is known to improve tissue viability, reduce ischemic injury by preventing cell swelling, interact with lipids in the cell membrane, and scavenge free radicals. OPS containing PEG20M also appears to blunt the immune response to a transplanted organ previously flushed with a PEG solution. Itasaka et al. *Transplantation* 57:645–648 (1994); and Tokunaga et al. *Transplantation* 54:756– 758 (1992). PEG20M has also been proposed to be effective when used only as a terminal rinse solution after a period of ice storage. Collins et al. (1992).

There is a need for an improved composition for use in OPS's and other aspects of preserving or restoring the function of cells, tissues or organs that displays improved storage stability under practical commercial conditions.

All references cited herein are hereby incorporated by reference in their entirety.

SUMMARY OF THE INVENTION

This invention encompasses biologically effective compositions of matter containing substantially linear polyethylene glycol (LPEG) and methods of use thereof. Specifically, it relates to organ protection, preservation and cardioplegia solutions and methods of use thereof in surgical operations on and transplantation of mammalian organs.

The invention encompasses a composition comprising a storage-stable organ preservation solution, comprising a biologically effective amount of substantially linear polyethylene glycol essentially free of decomposition products. In one embodiment of the organ preservation solution, the linear polyethylene glycol is present in a concentration in the range of from about 0.1% to about 20% by weight, preferablly in the range of from about 2% to about 15% by weight, and more preferably in a concentration of between about 7% and 8% by weight.

In one embodiment of the organ preservation solution the linear polyethylene glycol has an average molecular weight of greater than approximately 8,000 Daltons, and the linear polyethylene glycol is present in a concentration in the range of from about 2% to about 15% by weight.

In one embodiment of the organ preservation solution the linear polyethylene glycol has an average molecular weight in the range of approximately 20,000 to approximately 35,000 Daltons, preferably the linear polyethylene glycol has an average molecular weight of approximately 20,000 Daltons and is present in a concentration of between approximately 7% and approximately 8% by weight.

In another embodiment of the organ preservation solution the decomposition products are present in a concentration sufficiently low that four hour storage of isolated rabbit hearts with the composition results in less than about a 30% decrease in cardiac output.

In yet another embodiment, the organ preservation solution is storage-stable for at least about 12 months when stored anoxically in the absence of exposure to UV light at a temperature of about 4° C.

In an alternative embodiment of the present invention, a storage-stable aqueous solution for the preservation of organs comprises from about 0.1% to about 20% by weight of linear polyethylene glycol having an average molecular weight greater than approximately 8,000 Daltons and essentially free of decomposition products, further comprising an effective amount of any or all of the following additional components: (a) a buffer; (b) an impermeant anion; (c) a component providing phosphate; (d) a component providing potassium; (e) a component controlling cell swelling; and (f) a component providing magnesium. This composition may further contain additional components comprise any or all of the following: (a) NaOH; (b) Lactobionic acid; (c) $KH_2PO_4$; (d) KOH; (e) Raffinose; (f) $MgSO_4$; and (g) para-hydroxyanisole. Specifically, the additional components can comprise any or all of the following: (a) NaOH, about 5–125 mM; (b) Lactobionic acid, about 80–120 mM; (c) $KH_2PO_4$, about 5–50 mM, (d) KOH, about 5–125 mM; (e) Raffinose, about 25–35 mM; (f) $MgSO_4$, about 4–6 mM; and (g) para-hydroxyanisole, about 0.04 mM. The composition can further comprise any or all of the following additional components: (h) an antioxidant; (i) an iron chelator; and (j) a vasodilator. The composition can further comprise additional components selected from the group consisting of: (h) desferoxamine; and (i) nitroglycerin, or specifically wherein the additional components are selected from the group consisting of (h) Desferoxamine, 5–9 $\mu$M; and (i) Nitroglycerin, 2–3 mg/l.

In an additional embodiment, a method is provided for preparing a storage-stable aqueous solution for the preservation of organs, comprising the steps of: reducing the level of contaminating materials in a sample of linear polyethylene glycol; combining the linear polyethylene glycol in an organ preservation solution to obtain a final concentration of linear polyethylene glycol from about 0.1% to 20%; and storing the aqueous solution obtained under anoxic conditions in the absence of UV light.

In one embodiment of this method, the decomposition products are reduced by ultrafiltration. Alternatively, the decomposition products are reduced by dialysis. In another embodiment, the linear polyethylene glycol has an average molecular weight of greater than approximately 8,000 Daltons, and, preferably, a 10% by weight solution of said linear polyethylene glycol in distilled water has a conductivity of less than 20 microsiemens/centimeter ($\mu$S/cm).

Even more preferably, the linear polyethylene glycol comprises less than 2 mole-percent of aldehydes.

In an additional embodiment, a method for preserving an organ intended for transplantation is provided, comprising contacting the organ with a storage stable aqueous solution comprising from about 0.1% to 20% by weight of linear polyethylene glycol (PEG) having an average molecular weight greater than approximately 8,000 Daltons and essentially free of decomposition products. In a specific embodiment, the vascular system of the organ is flushed with the solution immediately prior to removal from a donor. Alternatively, the vascular system of the organ is contacted with a solution not containing PEG prior to removal from a donor and contacted with the solution containing PEG following removal from a donor. In one embodiment of the present invention, the organ is a heart.

In yet another embodiment of the present invention, a method for cardioplegia is provided comprising contacting a heart with an aqueous solution comprising from about 0.1% to 20% by weight of linear polyethylene glycol having an average molecular weight greater than approximately 8,000 Daltons and essentially free of decomposition products.

In still another embodiment of the present invention, a method for organ preservation is provided, comprising adding a biologically effective amount of substantially linear polyethylene glycol having an average molecular weight greater than approximately 8,000 Daltons and essentially free of decomposition products to the solution in which the organ is stored.

In yet another embodiment of the present invention, a method of organ preservation is provided, comprising administering to the host animal at least one intravenous bolus of a biologically effective amount of substantially linear polyethylene glycol having an average molecular weight greater than approximately 8,000 Daltons.

A method of treatment of a patient is also encompassed by the present invention, comprising administering to the patient a biologically effective amount of substantially linear polyethylene glycol having an average molecular weight greater than approximately 8,000 Daltons.

A method of treating an organ transplant recipient is also encompassed by the present invention, comprising administering to the recipient an amount of a composition comprising a substantially linear polyethylene glycol, having an average molecular weight greater than approximately 8,000 Daltons and essentially free of decomposition products, effective to enhance function of the transplanted organ.

DETAILED DESCRIPTION OF THE INVENTION

It has now been shown that previous OPS compositions, including PEG20M-Cardiosol, are not storage-stable. The present invention provides storage-stable compositions suitable for use in organ preservation and cardioplegia. The compositions are surprisingly storage stable and offer improved organ preservation activity. Although the compositions are preferably made by the methods described herein, they can also be made by any method known in the art. The compositions described herein comprise physiologically acceptable salts, substantially linear polyethylene glycol compounds and any other suitable OPS constituent.

By "LPEG" is meant a substantially linear polyethylene glycol, preferably having an average molecular weight of greater than approximately 8,000 Daltons, more preferably greater than approximately 8,000 to approximately 100,000 Daltons, even more preferably greater than approximately 8,000 to approximately 35,000 Daltons, and even more preferably approximately 20,000 to 35,000 Daltons. LPEG includes, but is not limited to, compositions comprising PEG20L. LPEGs in various molecular weights are available from a variety of commercial suppliers. Not all lots of commercially prepared PEG20L have the same activity in in vitro and in vivo assays. Given the knowledge in the art of organ transplantation and the examples provided herein, one of skill in the art can select an LPEG that is biologically effective for use in the present invention.

By "linear PEG" or "linear polymer" is meant a PEG molecule comprising a single subunit rather than more than one subunit joined together by molecular linkages such as the linkage that joins two PEG 8,000 to form PEG20M.

Those of ordinary skill in the art will appreciate that synthetic polymers such as PEG cannot be prepared practically to have exact molecular weights, and that the term "molecular weight" as used herein refers to the average molecular weight of a number of molecules in any given sample, as commonly used in the art. For example, a sample of PEG 2,000 might contain a statistical mixture of polymer molecules ranging in weight from, for example, 1,500 to 2,500 Daltons with one molecule differing slightly from the next over a range. In the case of PEG20L, by "having an average molecular weight of about 20,000 Daltons" is meant that individual linear polymers can vary in length, but the average molecular weight is about 20,000 Daltons. Specification of a range of molecular weight indicates that the average molecular weight can be any value between the limits specified, and can include molecules outside those limits. The molecular weight distribution of a PEG can be determined by any method known in the art, including, but not limited to, gel permeation chromatography (GPC), using, for example, a combination of columns to achieve resolution from 1,000,000 to 200 molecular weight. PEG standards from 100,000 to 1,400 molecular weight can be used for calibration.

It has now been found that a drawback of using the bisphenol epoxide linked PEG20M in OPS is its excessive vulnerability to oxidative damage. Excessive oxidative damage results in changes to the PEG structure and concomitant problems with instability of the OPS during storage and during use of the OPS to preserve organs. It is impractical to use a product that must be prepared immediately before use to cope with the products storage instability. Further, the decomposition of bisphenol epoxide linkers may release undesirable and potentially toxic substances.

PEG decomposes in solution. Without being bound to any one theory, it is believed that part of this decomposition results from oxidation that progresses through a number of oxidation products including: (1) an alkyl radical C.; (2) an alkoxy radical CO.; (3) a peroxy radical COO.; and (4) an organic hydroperoxide. It is believed that small molecular weight fragments may also be formed such as formate, methyl formate, formaldehyde, acetaldehyde, etc., all of which are here encompassed by the term "decomposition products".

By "storage-stable" is meant that the OPS containing LPEG is resistant to decomposition due to conditions of handling and storage. In a preferred embodiment of the present invention, the OPS containing the LPEG is storage-stable for at least about 12 months when stored anoxically in in the absence of exposure to UV light at a temperature of about 4° C. PEG20L is supplied as a white flake, and is readily soluble in water. The decomposition rate of PEG20L and other LPEGs is dependent on storage conditions including: (1) whether stored as a flake or in solution; (2) temperature; (3) exposure to light, especially UV light; and (4) the availability of oxygen. The compositions of the present invention are preferably storage-stable for at least about 12 months when stored anoxically in a fashion that prevents exposure to UV light and atmospheric oxygen, (including, but not limited to storage in a foil envelope) at a temperature of about 4° C.

By "anoxically" is meant an amount of oxygen that is less than either: the atmospheric level of oxygen; or, if the amount of oxygen is measured in solution, the level that would be present were the solution in contact with ambient air. Without being limited to one particular method of controlling oxygen levels, an anoxic condition can be obtained and maintained by continuous purging with argon or nitrogen gas, and then packaging in a gas-impervious container. For the present invention, the absence of oxygen need not be total. Preferably, it is below about 6% of the total gas present in the sample. More preferably, it is below about 1% of total gas present in the sample.

LPEG does not have the disadvantages of the previously preferred PEG20M. PEG20M has a high viscosity, in part because it contains some very highly linked, high molecular weight components. High viscosity in an OPS can make delivery of the OPS to some organs under certain circumstances difficult. For example, where rapid circulation of an OPS through an organ is desired for preservation, a lower viscosity OPS may be desired. Thus, the present invention contemplates that for some applications of OPS, lower viscosity PEGs may be preferred. PEG20M solutions may contain potentially toxic breakdown products of the bisphenol epoxide linker, which increase in amount during storage. The presence of the linker causes PEG20M solutions to readily clog filters, making it difficult to process PEG20M-Cardiosol heart preservation solution. PEG20M can also contain trace amounts of carbon disulfide and methylene chloride (at less than 10 parts per billion, as determined by mass spectrometry). The concentration estimates were based on the average responses for various organic compounds run under identical conditions. In addition, LPEG is more homogeneous than PEG20M.

By "organ preservation solution" (OPS) is meant an aqueous solution specifically designed to preserve organs. In one embodiment of the present invention the organ is the heart. The solutions are used in organ transplantation, and can also be used in cardioplegia during open heart surgery as a crystalloid solution or in blood cardioplegia. The OPS can also be used to flush the organ to be transplanted either prior to or after harvesting (removal from a donor), or both. Use of the OPS as a terminal rinse (flushing of the organ after harvesting) is preferred if the organ had been flushed previously with a solution not comprising PEG.

One consideration when designing an OPS is the permeabilities of the two main types of biological membrane, the cell membrane and the vascular endothelium. The cell membrane is permeable to water but relatively impermeant to most water soluble compounds and ionic species, regardless of their size. Osmotic pressure results when the total concentration of all dissolved impermeable species on one side of a water permeable membrane is different from that on the other. This discrepancy in solute concentration results in an equal and opposite discrepancy in water concentration with the net movement of water will be from the region of higher to lower solute concentration, resulting in an increase in pressure on the low solute side of the membrane.

Species which readily cross this membrane are either those which are small and lipid soluble, or amphipathic, and can thus dissolve in the hydrophobic core of the membrane, or those for which specific transport mechanisms are available, including, but not limited to, glucose, sodium or calcium channels and pumps. Many ionic and nonionic hydrophilic compounds can be used in an OPS to balance the osmotic pressure due to the intracellular components. "Basic Human Physiology" by Arthur C. Guyton, W. B. Saunders Company, Philadelphia (1977). For reasons of chemical and physiological compatibility some are of more utility than others.

In contrast to the cell membrane, the vascular endothelium is a barrier between the circulation and the extracellular fluid surrounding the parenchymal cells of individual organs. This barrier is composed of endothelial cells which normally maintain tight junctions between cells. The endothelial cell membrane has permeability characteristics similar to those of other cells. However, the cell-cell junctions are designed to act as pores which allow nutrients to pass into the extravascular space and receive cellular waste products from that space. As such, these pores are permeable to small molecular weight (generally less than approximately 1000 Dalton) hydrophilic compounds but impermeable to high molecular weight materials such as the proteins which are normal plasma constituents. Higher molecular weight agents then act by reducing the effective water concentration within the vasculature to maintain an osmotic pressure which ensures that fluid does not accumulate within the extravascular space.

Without being bound to any one theory or mechanism of action, it is believed that, in the OPS of the present invention, the large molecular weight hydrophilic species PEG acts as a relatively endothelium-impermeant osmotic component that acts in part to maintain a physiologically acceptable osmotic pressure.

The OPS comprising PEG20L is designated PEG20L-Cardiosol. Preferably, PEG20L-Cardiosol contains between about 0.1% and 20% by weight LPEG. More preferably, PEG20L-Cardiosol contains between about 2% and 15% by weight LPEG, even more preferably, PEG20L-Cardiosol contains between about 7% and 8%, and most preferably about 7.5% by weight PEG20L.

The OPS described herein can also contain effective amounts of: (a) an additive to adjust pH, such as NaOH, preferably about 5–125 mM, (or sufficient to result in pH of preferably about 7 to about 8); (b) an impermeant anion such as lactobionic acid, preferably about 80–120 mM; (c) a component providing phosphate such as $KH_2PO_4$, preferably about 5–50 mM; (d) a component providing potassium such as KOH, preferably about 5–125 mM, where the combined concentration of $KH_2PO_4$ and KOH is preferably 5–125 mM; (e) a component controlling cell swelling such as raffinose, preferably about 25–35 mM; or (f) a component providing magnesium such as $MgSO_4$, preferably about 4–6 mM.

Preferably, the OPS described herein contains between about 2% and about 15% by weight LPEG and can also contain: (a) NaOH, about 30–40 mM; (b) Lactobionic acid, about 100 mM; (c) $KH_2PO_4$, about 25 mM; (d) KOH, about 100 mM; (e) Raffinose, about 30 mM; or (f) $MgSO_4$, about 5 mM.

NaOH can be used to adjust pH of the solution to the desired level. Any other suitable base can also be used. Lactobionic acid is an impermeant anion which chelates calcium and iron. $KH_2PO_4$ and KOH provide potassium to arrest the heart (cardioplegia) and maintain the intracellular potassium concentration. $KH_2PO_4$ also provides phosphate for buffering, and KOH provides OH, which neutralizes lactobionic acid. Raftinose, which can be substituted with other impermeant non-electrolytes, controls cell swelling. Magnesium is an essential metal, a component in blood, which can compete with calcium at the receptor level in the heart to prevent an overload of calcium which can lead to stiffening of the cardiac muscle tissue.

Optionally, the organ preservation solution also contains effective amounts of any component known in the art of organ preservation. These include, but are not limited to, a component controlling redox potential such as glutathione at about 3 mM, and para-hydroxyanisole (PHA), desferoxamine (Des.), or nitroglycerin (NTG).

Glutathione protects against free radical injury to cells. PHA or other antioxidants can be introduced to reduce oxidative alteration of the polyethylene glycol. In one embodiment, the OPS of the present invention contains, optionally, 2 to 10 ppm of PHA. Des. is an iron chelator, believed to lower the concentration of free Fe in the OPS and the flushed heart. The OPS of the present invention contains, optionally, 5–9 $\mu$M of Des., more preferably 7.1 $\mu$M Des. NTG acts as a vasodilator due to generation of nitric oxide. NTG improves cardiac function of hearts tested with aging, relatively decomposed PEG solutions. The OPS of the present invention contains, optionally, 2–3 mg/L, more preferably 2.5 mg/L of NTG.

By "biologically effective amount" is meant a concentration of the component able to improve the ability of an OPS to preserve organs or a concentration able to preserve or restore cell, tissue or organ function. Preferably, LPEG is present in compositions of the present invention in a biologically effective amount and is essentially free of decomposition products.

Preferably, the OPS of the present invention contains between about 0.1% and 20% by weight LPEG. More preferably, the OPS of the present invention contains between about 2% and 15% by weight LPEG, even more preferably, the OPS of the present invention contains between about 7% and 8% by weight PEG20L, and most preferably, the OPS of the present invention contains about 7.5% by weight PEG20L.

By "essentially free" is meant that the levels of decomposition products in the LPEG solutions are sufficiently low such that four hour storage of isolated rabbit hearts with the composition results in less than about a 30% decrease in cardiac output.

A suitable assay for organ function is an ex-vivo heart perfusion circuit filled with oxygenated modified Krebs Henseleit solution at 37° C. The hearts are allowed 15 minutes of recovery while on retrograde Langendorff perfusion at a pressure of 100 cm $H_2O$. This is converted to a working heart mode for a 45-minute test period during which the LA (left atrium) pressure is kept at 16 cm $H_2O$ and the aortic outflow is connected to a column in which the overflow is set at 100 cm $H_2O$. Measurements of coronary and aortic flow rates (and aortic pressure in the case of poorly preserved hearts) are made and recorded at one hour and cardiac output is calculated. Wicomb et al. Transplantation Proceedings 21:1366–1368 (1989).

By "decomposition products" is meant the products produced when PEG (linked or unlinked) is oxidized or otherwise decomposed. The levels of these decomposition products can be reduced by ultrafiltration or dialysis. The progress of ultrafiltration or dialysis can be monitored by measuring conductivity of the solution. When ultrafiltration or dialysis is sufficient, conductivity generally drops below about 10 $\mu$S/cm. Where the PEG has not decomposed appreciably and does not contain amounts of impurities that effect its activity in an OPS, ultrafiltration may not be necessary.

Ultrafiltration can be performed using a Regenerated Cellulose Ultrafiltration Membrane or a Polyethersulphone Ultrafiltration Membrane or using other methods known in the art; dialysis can be performed using a Cellulose Acetate Hollow Fiber Dialyzer (Baxter Model CA 110) or using other methods known in the art. The membrane preferably has a molecular weight cut off of approximately 7,000–20,000 Daltons to allow removal of contaminating materials, including, but not limited to: oxidation products, ionic materials, metals and other contaminants. When OPS is prepared on a large scale, ultrafiltration is preferable to dialysis due to the relative speeds of processing large volumes. Preferably, ultrafiltration or dialysis consists of at least 1–2 changes of $H_2O$, or ultrafiltration or dialysis against at least a 1–2× volume of water. More preferably, ultrafiltration or dialysis consists of at least 3 changes of pure water, or ultrafiltration or dialysis against at least a 3× volume of water. Where a PEG contains high levels of decomposition products or other contaminants, it is preferred that ultrafiltration or dialysis is performed against sufficient volumes of water, or changes of water, to ensure that the contaminants are reduced to acceptable levels.

Screening steps are provided herein that guide one to determine whether a specific LPEG sample will be biologically effective in an OPS. Guidance in selection are provided by analyzing the following parameters: (1) Ionic Content; (2) Antioxidant Content; (3) Aldehyde Levels; (4) Cell Based Assay Performance; and (5) Organ Preservation Performance.

(1) Ionic Content

The ionic content of a solution of PEG can be evaluated as follows. A conductivity meter (available from many commercial sources, including Fischer Scientific, Pittsburgh, Pa.) is used to measure the conductivity of an 8 to 10% by weight solution of PEG20L in distilled water or water for injection. Measurements are repeated after three or four ultrafiltrations or dialyses with distilled water. The initial conductivity is roughly proportional to the age and state of decomposition of the PEG (data not shown). A recently manufactured PEG usually has a conductivity of around 10 $\mu$S/cm, and is virtually unchanged after dialysis. In contrast, an old more decomposed PEG (three to seven years old) may have a conductivity approaching 100 units, which falls to 10–20 $\mu$S/cm after dialysis. In the present invention, a 10% solution of PEG20L in distilled water has preferably a conductivity of less than 30 $\mu$S/cm, more preferably a conductivity of 10 to 20 $\mu$S/cm.

(2) Antioxidant Content

The levels of antioxidants present in the PEG can be evaluated by reverse phase HPLC (High Pressure Liquid Chromatography), for example, using a C18 column with 100% acetonitrile mobile phase at 1 mL/minute flow rate. In a preferred embodiment of the present invention, the PEG contains less than 500 parts per million (ppm) antioxidant prior to dialysis or ultrafiltration.

(3) Aldehyde Levels

The following test is described generally by Gad Avigad, in "A Simple Spectrophotometric Determination of Formaldehyde and Other Aldehydes: Application to Periodate-Oxidized Glycol Systems," Analytical Biochemistry 134:499 (1983), and has been modified as follows:

A solution of LPEG for testing is prepared by dissolving 1 g LPEG in 10 mL deionized water. 100 $\mu$L and 200 $\mu$L aliquots of this solution are transferred to borosilicate tubes. 100 $\mu$L of deionized water is then added to each 100 $\mu$L sample.

Calibration standards (200 $\mu$L each) consist of the following concentrations of a fresh formaldehyde solution: 0.0, 0.6, 1.9, 3.1, and 4.4 mg/L.

To each 200 $\mu$L solution of calibration standards and samples, prepared in triplicate in borosilicate tubes, 300 $\mu$L of a 1% 4-amino-3-hydrazino-5-mercapto-1,2,4-triazole (AHMT) solution in 1 M NaOH is added and vortexed to mix well. The reaction mixture is shaken at approximately 150 rpm on a rotary shaker at ambient temperature for 30 minutes. 500 $\mu$L of 0.2% sodium borohydride solution in 1 M NaOH is then added to stop each reaction, and vortexed to mix well. Each sample is transferred to a 1-mL polystyrene cuvette.

The spectrophotometer is calibrated and the absorbance of each standard/sample at 545 nm is measured to determine the approximate concentration of aldehyde present in the LPEG tested. In a preferred embodiment, PEGs containing aldehyde levels above 2 mole-percent are not used in methods of the present invention.

(4) Cell Based Assay Performance

An in vitro cardiomyocyte assay can be used to evaluate the biological effectiveness of LPEG.

The following assay is described in detail in Example 5. Cardiomyocytes from infant rats are prepared by trypsinization and mechanical disaggregation and resuspended in Modified Eagles Medium (MEM), 1×MEM vitamins (Gibco), 5% fetal bovine serum and 50 U/mL penicillin-G and pre-plated for 30 minutes to reduce contamination of non-myocytes. The non-adherent cardiac myocytes are separated and seeded in 35 mm dishes at a density of approximately $3.5 \times 10^5$ viable cells per mL. The cells are allowed to adhere for 16–24 hours in a 37° C./5% $CO_2$ humidified incubator.

Serum deprivation is performed by replacing the medium with fresh serum-free RPMI Media, whereas serum/glucose deprivation is performed using glucose-free RPMI. As a model of ischemia, cultures in serum and glucose free RPMI are placed in an airtight chamber and the latter is continuously perfused with oxygen-free gas overlay of 95% $N_2$/5% $CO_2$ for 8 hours at 37° C. To model reperfusion of the ischemic cells, 10% fetal bovine serum, 2 g/L of glucose are added and the cultures are returned to a normal oxygen gas overlay (37° C./5% $CO_2$) in a humidified incubator for 16 hours.

To investigate the biological efficacy of a particular sample of LPEG, LPEG is added to cells in serum free medium at the beginning of cytotoxic treatment.

Because cardiomyocytes are terminally differentiated non-dividing cells, viability is then determined by measurement of the decrease in the relative number of adherent cells. Adherent cardiomyocytes are collected from culture dishes using 0.25% Trypsin/0.05% EDTA and counted on Coulter Counter ZM and Coulter Channelyzer 256.

In a preferred embodiment of the present invention, the LPEG to be used in the OPS will display biological activity in that it reduces the level of cardiomyocyte cell death following serum deprivation when compared to control cells not treated with the LPEG.

(5) Organ Preservation Performance

Direct testing of the ability of various OPS compositions to preserve organs can also be performed on animal organs, as is well-known in the art. Cardiac Output (CO) and organ failure rates are typically measured. See, for example, Wicomb et al. *Transplantation* 47:733–734 (1989) and other documents cited herein. For example, the rabbit heart model described herein measures cardiac output of rabbit hearts that have been treated with a single flush of LPEG. These hearts are functionally evaluated on an ex-vivo perfusion circuit filled with oxygenated modified Krebs Henseleit solution at 37° C. The hearts are allowed 15 minutes of recovery while on retrograde Langendorff perfusion at a pressure of 100 cm $H_2O$. This is converted to a working heart mode for a 45-minute test period during which the LA (left atrium) pressure is kept at 16 cm $H_2O$ and the aortic outflow is connected to a column in which the overflow is set at 100 cm $H_2O$. Measurements of aortic pressure, coronary and aortic flow rates are made and recorded at one hour and cardiac output is calculated. Wicomb et al. *Transplantation Proceedings* 21:1366–1368 (1989In a preferred embodiment, the LPEG results in less than about a 30% decrease in cardiac output as tested in rabbit hearts, as compared with the function of an untreated heart that has not been stored.

The decomposition rate of PEG as a function of time can also be determined by thermal gravimetric analysis, a technique commonly known in the art.

Not all brands of PEG20L are effective for use in the present invention. Thus, PEG20L is preferably tested as described herein to determine whether it is suitable for use in the present invention.

Preferably, the levels of decomposition products in an OPS of the present invention are low enough not to cause a 30% decrease in cardiac output of a rabbit heart after 4 hour storage.

An alternative strategy to the addition of antioxidants to block oxygen free radical damage is the introduction of iron chelators during preservation or reperfusion. Ferreira et al. *J. Thorac. Cardiovasc. Surg.* 100:708 (1990). A low concentration of desferoxamine has been proposed to reduce oxidative stress, provided strong reducing agents are not present to catalyse redox cycling of the ferrous/ferric desferoxamine complex. Borg et al. *J. Free Radical Biol. Med.* 2:237 (1986). The incorporation of these antioxidants in the OPS is encompassed by the present invention.

In some cases it may be desirable to perform internal delivery of compositions of the present invention in a localized area of the body, organ or tissue. The present invention encompasses methods of delivery including, but not limited to, delivery by catheter inserted into a vessel. The present invention additionally encompasses solutions suitable for flushing, perfusion, and storage of organs and tissues prior to or during transplantation. Such solutions are described in Chien et al. (1993) "Hibernation Induction Trigger for Organ Preservation" in Medical Intelligence Unit, R. G. Landes Co. Austin, Tex.

The compositions are also suitable for use in organ transplantation during all phases of transplantation. The compositions can be used to prepare the organ by administering an amount of the compositions to the donor effective to stabilize or preserve the organ. The organ can be perfused and/or preserved in OPS's containing the compositions. The organ recipient can then be administered an amount of the compositions effective to enhance organ stability and function.

The compositions are also particularly suitable for use in protecting organs during routine open heart cardioplegic applications, or closed heart cardioplegic applications such as those described in U.S. Pat. Nos. 5,536,251; 5,618,306; 5,618,307; 5,626,607. and 5,613,937, wherein surgery is performed on the heart through small incisions rather than by exposing the entire chest cavity.

The invention further provides methods of preserving cells during the culture or maintenance of mammalian organs, tissues, and cells by the addition of an effective amount of LPEG to any media or solutions used in the art of culturing or maintaining mammalian organs, tissues, and cells.

The following examples are provided to illustrate but not limit the claimed invention.

EXAMPLE 1

The Effects of Substituting PEG20L for PEG20M in a Heart Preservation Solution

The effects of the substitution of PEG20L for PEG20M in a heart preservation solution was tested. Rabbit hearts were treated and Cardiac Output (CO) measured as described previously in Wicomb et al. *J. Surg. Res.* 40:276 (1986); and Wicomb et al. *Transplantation* 48:6–9 (1989), and as described below.

| | CARDIAC OUTPUT (mL/min) | | |
|---|---|---|---|
| Solution used | Flush Only (0 Hour) | 4 Hour | 24 Hour |
| PEG20M-Cardiosol | 171 ± 17 n = 14 | 164 ± 31 n = 8 | 212 ± 48 n = 10 |
| PEG20L-Cardiosol | 312 ± 24 n = 4 | 327 ± 30 n = 20 | 330 ± 32 n = 4 |
| UW solution | 282 ± 5 n = 4 | 256 ± 65 n = 12 | 88 ± 32 n = 2 |
| No solution | 285 ± 32 n = 4 | | |

60 minute cardiac output (mL/min) data following zero, 4 and 24 hours ice storage of rabbit hearts using PEG20M-Cardiosol, PEG20L-Cardiosol, University of Wisconsin (UW) solution or no solution. n indicates the number of rabbit hearts used.

The data clearly indicate that the use of PEG20L-Cardiosol substantially improves the cardiac output of rabbit hearts compared to either of the other two solutions, following 24 hours ice storage.

EXAMPLE 2

The Effects of Substituting PEG20L for PEG20M in a Heart Preservation Solution

| Solution used | CARDIAC OUTPUT (mL/min) | | |
|---|---|---|---|
| | 5% | 8% | 10% |
| PEG20M-Cardiosol | 136 ± 19.4 n = 13 | NT | 212 ± 8 n = 30 |
| PEG20L-Cardiosol | NT | 256 ± 12.3 n = 44 | NT |

NT, not tested. n indicates the number of rabbit hearts tested. Cardiac output was tested after 60 minutes on the working heart column following 24-hour storage on ice, as described in Wicomb et al. J. Heart Lung Transplantation 13:891–894 (1994).

The data clearly indicate that the use of 8% PEG20L in an OPS improves the cardiac output of rabbit hearts compared to PEG20M-Cardiosol comprising 5% or 10% PEG20M.

EXAMPLE 3

In order to determine the biological effectiveness of the claimed invention, the following experiment was performed. The cell assay is described in PCT Publication Nos. WO 94/25621 and WO 95/15173. Briefly, the cells, C3H/10T1/2 clone 8, were assayed at 50–80% confluence, during exponential growth phase when cell cycle position is randomly distributed with no cells arrested in $G_o$, and in quiescence. Exponential growth phase was assured by seeding at 2000 cells per 1 mL (5 mL for a 60 mm culture plate) five days prior to the beginning of the experiment. At T=0, cultures were transferred to serum-free medium containing the indicated PEG concentration, as a model of ischemia. Assays were performed in triplicate or quadruplicate. Analyses of the cell responses were made between 18 and 28 hours of serum deprivation with test material in Basal Medium Eagle's (BME) culture medium. Two assays were performed on each cell culture plate consisting of differential cell counts.

1. All non-adherent or loosely adherent cells were removed from the culture dish and counted by appropriate techniques, typically counting by electronic particle counting instrument. These were the serum deprived released cells (SDR), released by the action of cultivation in serum-free medium.

2. The remaining adherent cells (ADH) were exposed to a buffered, typically pH 7.3, balanced salt solution such as Hanks Balanced Salt Solution without calcium and magnesium salts containing 0.05% trypsin and 0.53 mM ethylene diaminetetraacetic acid (EDTA). Each culture was incubated at either room temperature or 37° C. on a rocking platform to ensure uniform distribution of the trypsin reagent over the culture surface. After a standardized period of time, typically 10 minutes, the released cells were removed from each culture dish and measured by the same means as described above, typically electronic particle counting. This ADH cell count was comprised of both trypsin resistant and trypsin sensitive cells as described in PCT Publication No. WO 94/25621.

Figure 1:
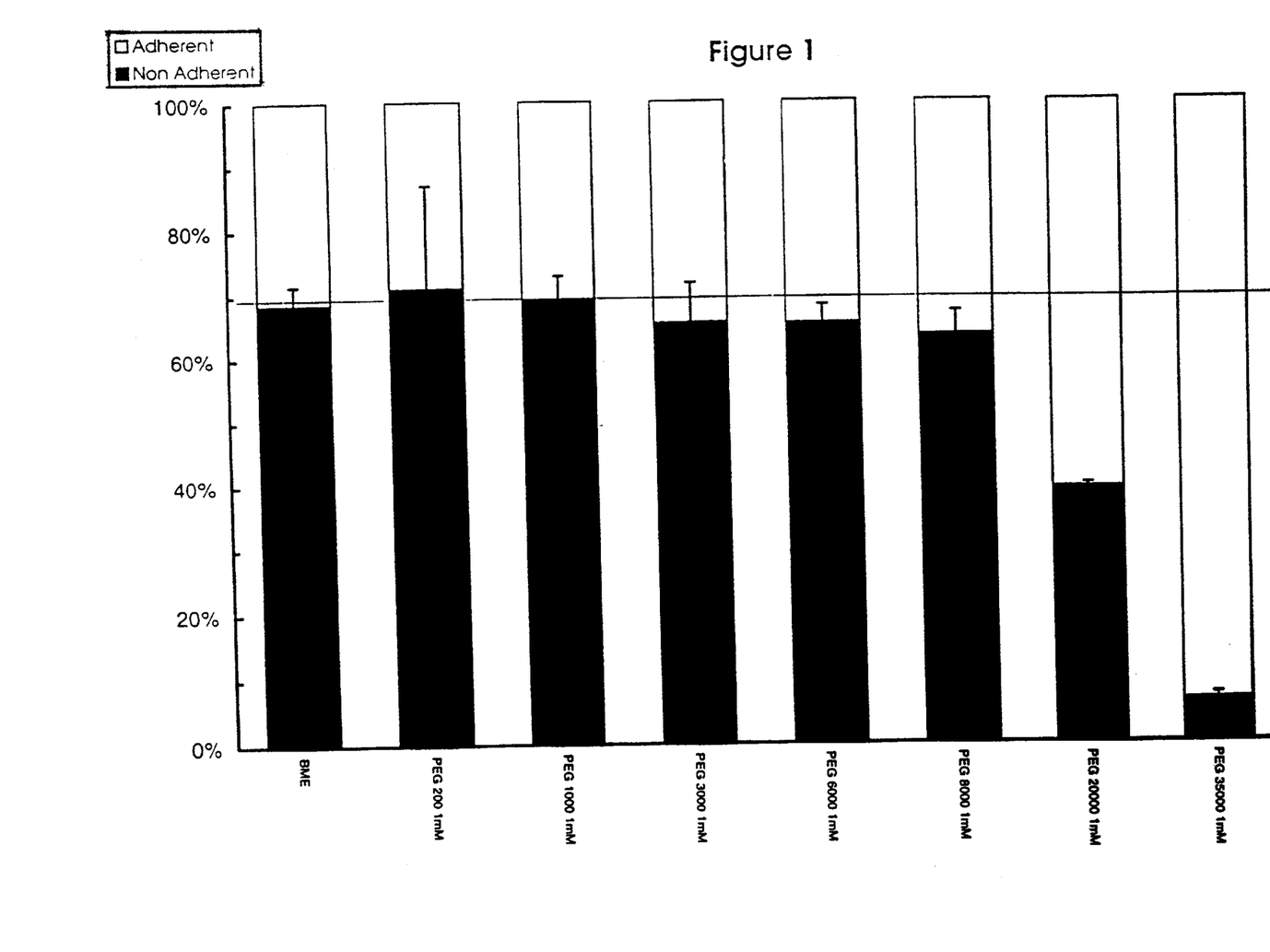
FIG. 1 is a bar graph depicting the effect of LPEG molecular weight on protection of C3H/10T1/2 cells from serum deprivation at a concentration of 1 mM. LPEG of molecular weights 200, 1,000, 3,000, 6,000, 8,000, 20,000 and 35,000 were used. The open section of the bars represents adherent, viable cells and the solid section of the bars represents non-adherent, dead cells.
Figure 2:
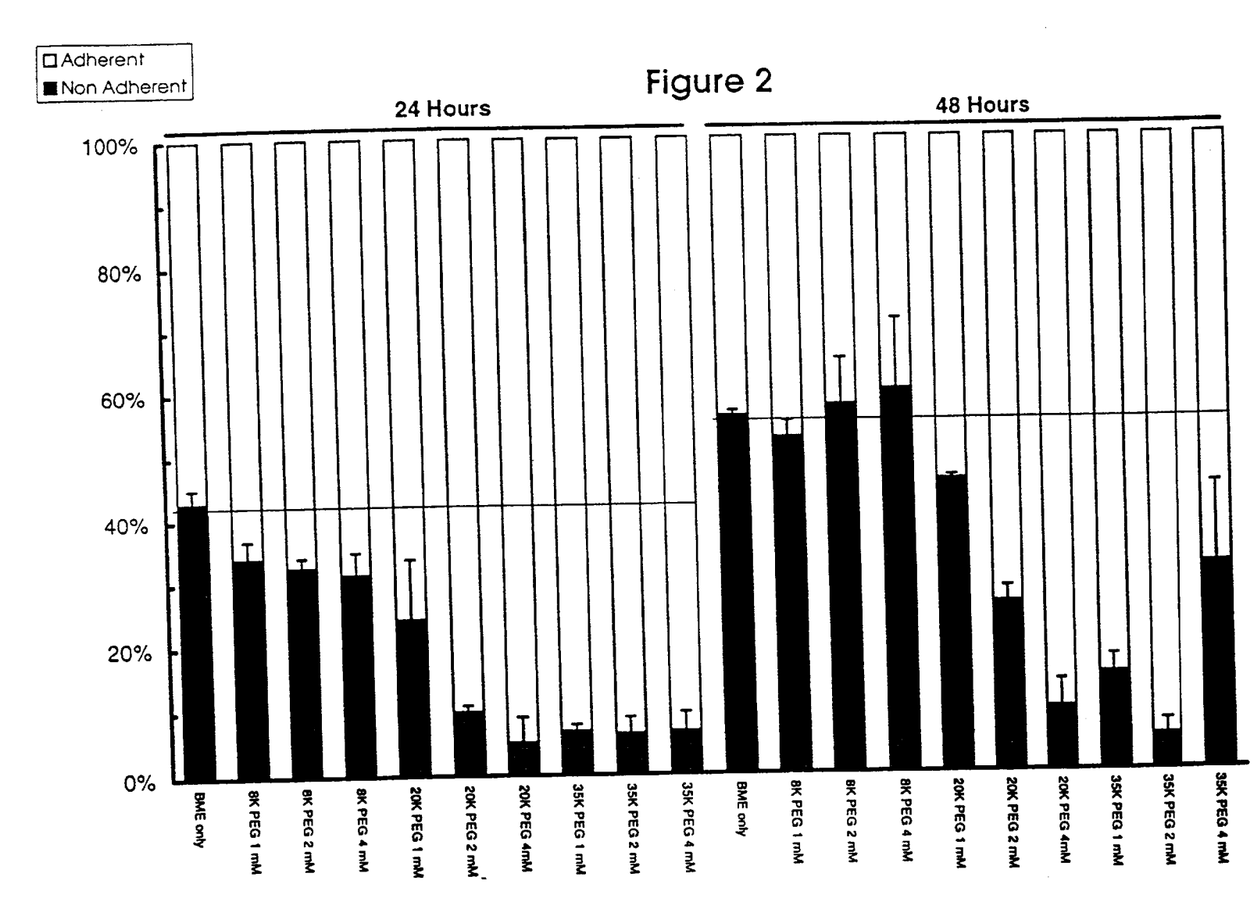
FIG. 2 is a bar graph depicting the effect of PEG concentration and molecular weight on protection of C3H/10T1/2 cells from serum deprivation over 24 and 48 hours. PEG of molecular weights 8,000, 20,000 and 35,000 were used at concentrations of 1, 2 and 4 mM. The open section of the bars represents adherent, viable cells and the solid section of the bars represents non-adherent, dead cells.

The results obtained are depicted in FIGS. 1–2. It is clear from the results that LPEG having molecular weights above 8,000 display cell protection activity.

EXAMPLE 4

Preparation of PEG20L-Cardiosol

An OPS of the present invention is substantially produced as described in U.S. Pat. No. 4,938,961, issued Jul. 3, 1990, to Collins et al., with the following or additional modifications:

A solution comprising the following ingredients is prepared:
(a) NaOH, about 5–125 mM,
(b) Lactobionic acid, about 80–120 mM;
(c) $KH_2PO_4$, about 5–50 mM;
(d) KOH, about 5–125 mM;
(e) Raffinose, about 25–35 mM;
(f) $MgSO_4$, about 4–6 mM; and
(g) optionally, PHA, about 0.04 mM;
(h) optionally, Glutathione, about 3 mM.

PEG20L, having an average molecular weight of greater than approximately 8,000 Daltons, preferably in the range of greater than approximately 8,000 to approximately 35,000 Daltons, and most preferably approximately 20,000 Daltons, is stored anoxically in the absence of UV light at a low temperature as described herein.

The PEG20L can be dissolved in water and ultrafiltered or dialysed as described herein. Evaluation of ionic content, antioxidant content and aldehyde levels, or any combination of these tests can be performed to determine the level of decomposition products and other undesirable components in the LPEG. Ultrafiltration or dialysis is preferred for LPEG solutions that contain more than 1.0 mole-percent aldehyde according to the aldehyde assay described herein.

Upon a demonstration from these methods that the PEG20L is suitable for the present invention, PEG20L (preferably at a final concentration of between about 0.1% and about 20%, more preferably between about 2% and about 15%, even more preferably, about 7–8 %, most preferably about 7.5 % by weight) is added to the solution. Optionally, PHA, Des., or NTG, or any combination of these, can be added. The solution is then stored under anoxic conditions as described above.

Direct testing of the ability of various OPS compositions to preserve organs can also be performed on animal organs, as is well-known in the art and described herein. Cardiac Output (CO) and organ failure rates are typically measured. See, for example, Wicomb et al. *Transplantation* 47:733–734 (1989) and documents cited herein.

The PEG20L-Cardiosol solution described in this example can be used for organ preservation as a perfusate in a process in which the perfusate is flowed through the circulatory system of the organ, and can also be used for cardioplegia applications.

EXAMPLE 5

In vitro Cardiomyocyte Assays

Cardiomyocytes were prepared from hearts of day-old Sprague Dawley rats by trypsinization and mechanical disaggregation (Simpson, (1985)) Circ. Res. 56:884–894. The cells were resuspended in Modified Eagles Medium (MEM), 1×MEM vitamins (Gibco), 5% fetal bovine serum and 50 U/mL penicillin-G and pre-plated for 30 minutes to reduce contamination of non-myocytes. The non-adherent cardiac myocytes were separated and seeded in 2 mL in 35 mm dishes at a density of $3.5 \times 10^5$ viable cells per mL. The cells were allowed to adhere for 16–24 hours in a 37° C./5% $CO_2$ humidified incubator.

Cardiomyocyte Treatment

For serum deprivation, the medium was replaced with fresh serum-free RPMI Media, whereas serum/glucose deprivation was performed using glucose-free RPMI. As a model of ischemia, cultures in serum and glucose free RPMI were placed in an airtight chamber and the latter was continuously perfused with oxygen-free gas overlay of 95% $N_2$/5% $CO_2$ for 8 hours at 37° C. To model reperfusion of the ischemic cells, 10% fetal bovine serum, 2 g/L of glucose were added and the cultures were returned to a normal oxygen gas overlay (37° C./5% $CO_2$) in a humidified incubator for 16 hours.

To investigate effect of LPEG on cell death, LPEG was added to cells in serum free medium at the beginning of cytotoxic treatment.

Measurement of Cell Death

Because cardiomyocytes are terminally differentiated non-dividing cells, viability was determined by measurement of the decrease in the relative number of adherent cells. The measurement of non-adherent cells was found to be less reproducible because of their rapid lysis following release from adhesion substrate. Adherent cardiomyocytes were collected from culture dishes using 0.25% Trypsin/0.05% EDTA and counted on Coulter Counter ZM and Coulter Channelyzer 256.

Results

Figure 3:
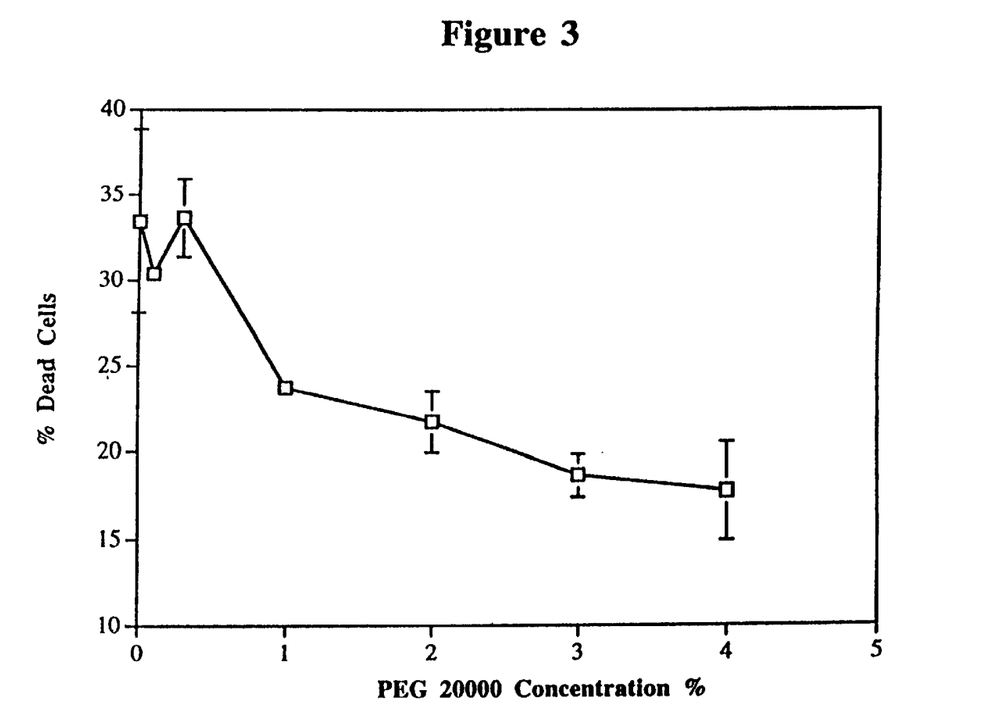
FIG. 3 is a graph depicting the prevention of cardiomyocyte death induced by serum/glucose deprivation by LPEG of MW 20,000 at different concentrations.
Figure 4:
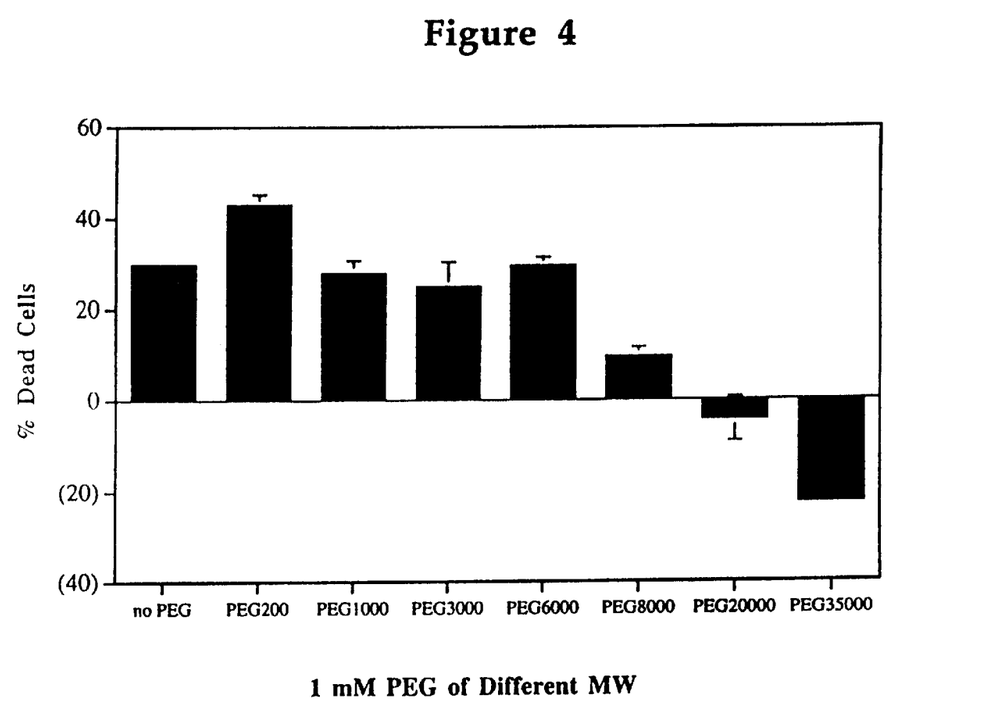
FIG. 4 is a bar graph depicting the prevention of cardiomyocyte death induced by serum/glucose deprivation by 1 mM LPEG of different molecular weights relative to cells maintained in complete serum.
Figure 5:
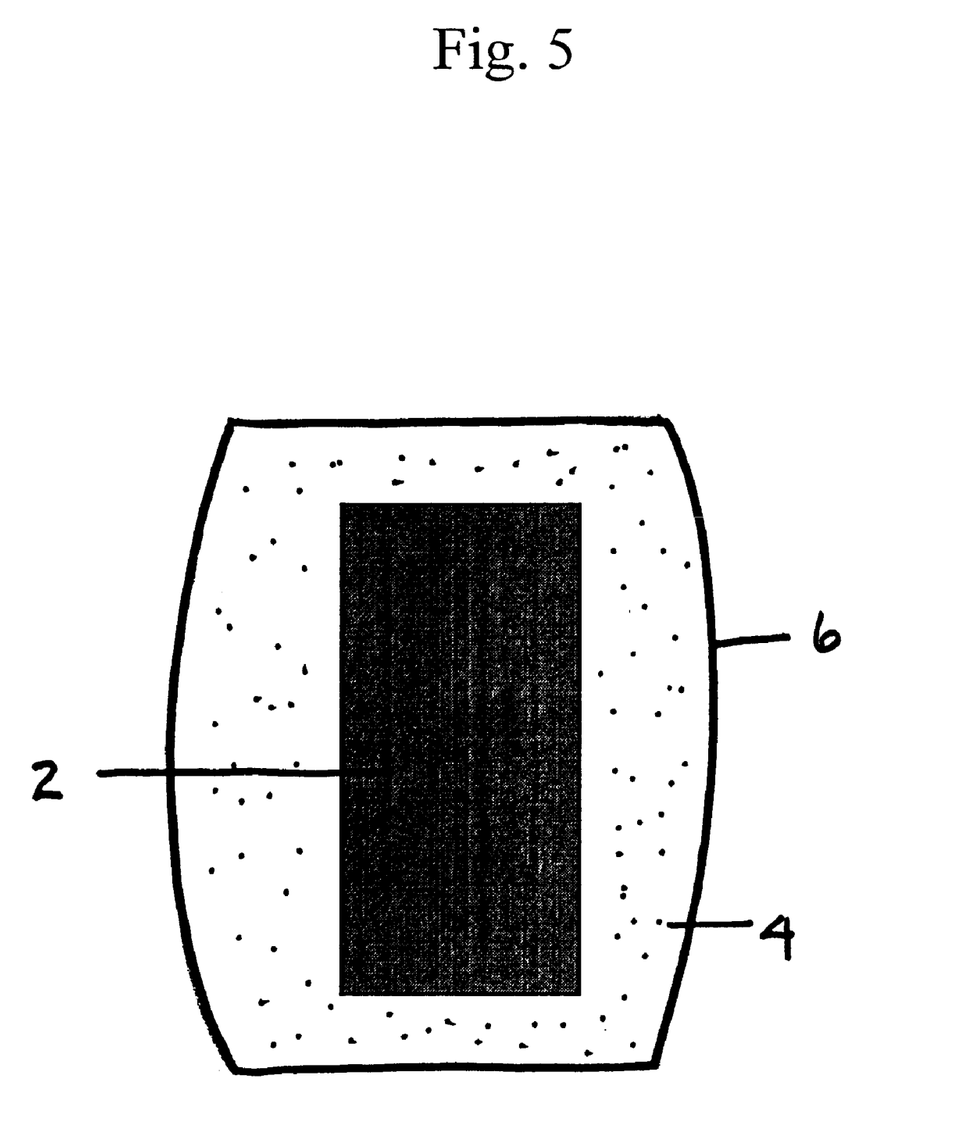
FIG. 5 illustrates one system for storing a linear polyethylene glycol solution, wherein reference number (2) is the LPEG solution, reference number (4) is the inert gas, and (6) is the foil envelope, which is both a light- and gas-impermeable container.

1. At concentrations of 1% and higher, 20,000 Dalton PEG partially prevents cardiomyocyte death induced by serum/glucose deprivation (FIG. 3).
2. LPEGs with molecular weight 200–6,000 Dalton did not protect cardiomyocytes from serum/glucose deprivation induced cell death in this assay. LPEG 8,000 show very little protection of cardiomyocytes. Significant protection of cardiomyocytes is seen with molecular weights of LPEG above 8,000. (FIG. 4).

It is clear from these results that LPEG at various concentrations and molecular weights is able to preserve or restore heart cell function.

Although the foregoing invention has been described in some detail by way of illustration and example for purposes of clarity and understanding, it will be apparent to those skilled in the art that certain changes and modifications can be practiced. Therefore, the description and examples should not be construed as limiting the scope of the invention, which is delineated by the appended claims.

What is claimed is:

1. A system for storing a stable polyethylene glycol solution comprising:
    (a) linear polyethlene glycol (LPEG) solution, wherein the LPEG has an average molecular weight of greater than 8,000 Daltons; and
    (b) a means for preventing light exposure to the LPEG solution.
2. The system of claim 1, wherein the means for preventing light exposure is a light impermeable container.
3. The system of claim 2, wherein the light is UV light.
4. The system of claim 1, wherein the light impermeable container is a foil envelope.
5. The system of claim 4, wherein the tight impermeable container contains an inert gas.
6. The system of claim 5, wherein the inert gas is argon or nitrogen.
7. The system of clam 1, wherein the system further comprises a gas-impermeable container.
8. The system of claim 7, wherein the gas-impermeable container is substanially impermeable to oxygen.
9. A system for storing a stable polyethylene glycol solution comprising:
    (a) a substantially linear polyethylene glycol (LPEG) solution, wherein the LPEG has an average molecular weight of greater than about 8,000 Daltons; and
    (b) a means for storing the LPEG solution anoxically in the absence of exposure to UV light.
10. The system of claim 9, wherein said LPEG, solution is stored at a temperature of about 4° C.
11. A system for storing a stable polyethylene glycol solution comprising:
    (a) a substantially linear polyethylene glycol (LPEG) solution, wherein the LPEG, has an average molecular weight of greater than about 8,000 Daltons;
    (b) a a foil envelope for preventing UV light exposure to the LPEG solution, wherein said foil envelope contains an inert gas selected from the group consisting of argon and nitrogen; and
    (c) a gas-impermeable container, wherein the gas-impermeable container is substantially impermeable to oxygen.

* * * * *